United States Patent
Ramarajan et al.

(10) Patent No.: US 11,710,572 B2
(45) Date of Patent: Jul. 25, 2023

(54) EXPERIENCE ENGINE-METHOD AND APPARATUS OF LEARNING FROM SIMILAR PATIENTS

(71) Applicant: Navya Network Inc., Cambridge, MA (US)

(72) Inventors: Naresh Ramarajan, Tujunga, CA (US); Gitika Srivastava, Cambridge, MA (US)

(73) Assignee: Navya Network, Inc., Cambridge, MA (US)

( * ) Notice: Subject to any disclaimer, the term of this patent is extended or adjusted under 35 U.S.C. 154(b) by 658 days.

(21) Appl. No.: 15/758,988

(22) PCT Filed: Sep. 9, 2016

(86) PCT No.: PCT/US2016/051036
§ 371 (c)(1),
(2) Date: Mar. 9, 2018

(87) PCT Pub. No.: WO2017/044802
PCT Pub. Date: Mar. 16, 2017

(65) Prior Publication Data
US 2020/0286599 A1 Sep. 10, 2020

Related U.S. Application Data (60) Provisional application No. 62/217,771, filed on Sep. 11, 2015.

(51) Int. Cl.
*G16H 50/70* (2018.01)
*G16H 10/60* (2018.01)
(Continued)

(52) U.S. Cl.
CPC ............. *G16H 50/70* (2018.01); *G06F 16/22* (2019.01); *G16H 10/60* (2018.01); *G16H 50/20* (2018.01); *G16H 70/20* (2018.01)

(58) Field of Classification Search
CPC ......... G16H 10/60; G16H 50/20; G06F 16/22
See application file for complete search history.

(56) References Cited

U.S. PATENT DOCUMENTS

| | | | |
|---|---|---|---|
| 8,060,178 B2 | 11/2011 | Zhou et al. | |
| 8,930,223 B2 * | 1/2015 | Friedlander | G06Q 50/24 705/3 |

(Continued)

FOREIGN PATENT DOCUMENTS

| | | | | |
|---|---|---|---|---|
| WO | WO 2015/062897 A1 | 5/2015 | | |
| WO | WO-2015062897 A1 * | 5/2015 | ............. | G16H 40/67 |

OTHER PUBLICATIONS

McMurray et al., Ontological modeling of electronic health information exchange, 56 J of Biomedical Informatics 169-178 (Aug. 2015) (Year: 2015).*

(Continued)

*Primary Examiner* — Fonya M Long
*Assistant Examiner* — Jordan L Jackson
(74) *Attorney, Agent, or Firm* — Nutter McClennen & Fish LLP (57) ABSTRACT

The present solution covers identifying a recommended treatment for a patient based on records of similar patients, wherein the similarities are non-obvious and non-linear. The solution generates a similarity map that minimizes the variance of elements records among a curated group of patients, and this similarity map is used to find the patients who are most similar to an untreated patient.

20 Claims, 2 Drawing Sheets

(51) Int. Cl.
  *G16H 50/20* (2018.01)
  *G06F 16/22* (2019.01)
  *G16H 70/20* (2018.01)

(56) References Cited

U.S. PATENT DOCUMENTS

| | | | |
|---|---|---|---|
| 8,977,574 B2 | 3/2015 | Jung et al. | |
| 2008/0162183 A1 | 7/2008 | Sachanandani et al. | |
| 2008/0201280 A1 | 8/2008 | Martin et al. | |
| 2009/0292557 A1 | 11/2009 | Sirohey et al. | |
| 2011/0092552 A1* | 4/2011 | Svensson | A61K 31/202 514/356 |
| 2011/0217270 A1* | 9/2011 | Cavanagh, III | A61P 35/00 424/93.7 |
| 2013/0226612 A1 | 8/2013 | Carmeli et al. | |
| 2015/0161331 A1* | 6/2015 | Oleynik | G16H 10/60 705/3 |
| 2017/0124269 A1* | 5/2017 | McNair | G16H 10/60 |
| 2018/0365337 A1* | 12/2018 | Sexton | G06F 16/26 |

OTHER PUBLICATIONS

Meystre et al., Extracting Information from Textual Documents in the Electronic Health Record: A Review of Recent Research, 17(01) Yerb Med Inform 128-144 (Year: 2008).*

Wang and Tansel, Composite Ontology-Based Medical Diagnosis Decision Support System Framework, 13(2) Communications of the IIMA 43-52 (Year: 2013).*

International Searching Authority, Notification of Transmittal of the International Search Report and the Written Opinion of the International Searching Authority, or the Declaration, PCT/US16/51036, 13 pages, dated Nov. 10, 2016.

Supplementary European Search Report for European Patent Application No. 16845156, dated Apr. 5, 2019 (9 pages).

Bar-Hillel, A. et al., "Learning Distance Functions using Equivalence Relations," Proc. International Conference on Machine Learning (ICML), 2003, pp. 11-18.

Examination Report for European Patent Application No. 16845156. 5, dated May 13, 2020, 11 pages.

Examination Report for Indian Patent Application No. 201817012589, dated Feb. 2, 2021, 7 pages.

Shental, N. et al., "Adjustment Learning and Relevant Component Analysis," Proc. European Conference on Computer Vision (ECCV), 2002, pp. 776-790.

Sorci, M. et al., "Fisher's Discriminant and Relevant Component Analysis for Static Facial Expression Classification," 15th European Signal Processing Conference (EUSIPCO), 2007, pp. 115-119.

Tsang, I. W. et al., "Kernel Relevant Component Analysis For Distance Metric Learning," International Joint Conference on Neural Networks, 2005, pp. 954-959.

Xing, E. et al., "Distance Metric Learning, with Application to Clustering with Side-Information," Advances in Neural Information Processing Systems, 2002, 8 pages.

Examination Report for Canadian Patent Application No. 2,997,354, dated Nov. 9, 2022, 3 pages.

Extended European Search Report for European Patent Application No. 22198396.8 dated Dec. 21, 2022, 11 pages.

* cited by examiner

EXPERIENCE ENGINE-METHOD AND APPARATUS OF LEARNING FROM SIMILAR PATIENTS

RELATED APPLICATION

This application claims priority to U.S. Provisional Application No. 62/217,771, entitled "Experience Engine-Method and Apparatus of Learning from Similar Patients" and filed Sep. 11, 2015, which is hereby incorporated by reference in its entirety.

TECHNICAL FIELD

The disclosure generally relates to systems and methods for facilitating medical decisions, such as identifying and selecting treatment recommendations for an individual patient based on groups of patients who are "similar", according to unconventional understandings of similarity.

BACKGROUND

Decision making in medicine, whether related to choice of treatments, diagnostics, other interventions, or selection of experts/hospitals, may be driven by data in a quantitative manner. Conventional methods of decision making may combine the conclusions of published medical research evidence from high quality clinical trials with patient preference and expert review in order to output suggested treatment plans for individuals.

For many patients, however, the combination of evidence and guidelines do not provide any decisions. Moreover, the evidence and guidelines are focused on common groups of patients for whom large scale clinical trials are available. Thus, the extent to which the treatment plans account for particular patients may be limited.

SUMMARY OF THE EMBODIMENTS

In a first aspect of the invention, a method selects a treatment for a patient based on a group of patients falling within a predetermined distance of a similarity map of data elements. The method includes storing, in a database, records for patients. Each record includes a first plurality of data elements regarding at least one medical condition and treatment of its respective patient, and a second plurality of data elements. Each data element in the second plurality corresponds to an additional medical condition of the respective patient that has been inferred from data elements in the first plurality of data elements. The method also includes receiving, by a server system, a context for treating to an untreated patient and a record of the untreated patient. The method also includes identifying, by the server system, a group of patients. Each patient in the group received treatment in the same context as the untreated patient.

The method also includes generating, by the server system, a similarity map that minimizes the variance of data elements among the group of identified patients. The method also includes determining, by the server system, similarity distances between the untreated patient and each patient in the group by applying the similarity map to data elements from the record of the untreated patient against data elements for each patient in the group. The method also includes selecting, by the server system, patients from the group that are within a predetermined similarity distance of the untreated patient. The method also includes identifying, by the server system, a treatment from the treatments received by the selected patients to recommend to the untreated patient.

In some embodiments, the first plurality of data elements may include conditions about the patient, observations about the patient, test results about the patient, clinical findings of the patient, obtained imaging about the patient, pathological findings of the patient, prior diagnosis, planned diagnostic interventions, prior therapeutic interventions, planned therapeutic interventions, morbidities, side effects of administered therapies, name of an expert physician, name of a hospital, and any combination thereof.

The method may include storing, for the record of the patient, the second plurality of data elements as logical combinations of terms using Boolean operators, nested hierarchies, or directed acyclical graphs. The method may include retrieving, by the server system, inference definitions from storage; and applying, by the server system, the inference definitions to the first plurality of data elements for a record to derive interconnected terms that are stored as the second plurality of data elements.

The method may include receiving a clinical diagnosis, an objective for treatment, a procedural timing, or any combination thereof. The objective for treatment may be curative, control, or palliative. The procedural timing for treatment may be primary, adjuvant, or neoadjuvant.

The method may include identifying, by the server system, a group of patients, wherein each patient in the group has a same value for a data element in a respective record of the patient. Each patient in the group may have received a treatment recommendation from the same expert. The method may include constraining, by the server system, the group of patients to patients with values of additional data elements in common until a number of patients in the group reaches a minimum size.

The method may include identifying, by the server system, a set of data elements to use in the similarity map by performing relevant component analysis on data elements for the group of patients to learn non-linear similarities between data elements. The method may include generating a locus of the group of patients, the locus representing average values across data elements for the group; and summing a function of distances between the locus and each patient in the group of patients.

The method may include selecting the treatment most common among the selected patients, or selecting the treatment at random among the treatments received by the selected patients.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

The systems and methods of this disclosure receive an untreated patient's record (e.g., including a medical record) and provides a recommendation tailored to the particular patient. Using a structured ontology developed by the inventors, a database that stores records for treated patients according to the inventors' ontology, and techniques that discover previously unappreciated similarities between groups of treated patients, illustrative embodiments of the invention enable previous treatment decisions to be harnessed on behalf of an untreated patient. The recommendations may be for treatments, expert physicians, hospitals, etc. Furthermore, the recommendations may be either positive or negative endorsements of particular treatments, physicians, or hospitals, etc. Although examples herein may be described with respect to recommending treatments for an untreated patient, the disclosure may be modified to enable other types of recommendations.

Advantageously, the systems and methods may leverage particular expert physicians' years of experience, especially when databases store decisions by these experts over a period of time. However, not all expert physicians are experienced. An experienced expert intuitively retrieves patterns from his/her vast "experience database" of patients that he/she has treated in the past. Recommending treatment decisions for patients with rare or complex diseases requires deep clinical reasoning from past experience. However, such expertise can be limited to tertiary care medical centers. For rare or uncommon diseases requiring multi-disciplinary coordinated care, such as most cancer care, the amount of experience from patient volume and complexity that accumulates in specialized tertiary care centers is unparalleled in any single physician's office outside of these settings. Patients who receive their treatment planning in specialized centers tend to have better outcomes than patients who receive care at their local treatment facilities.

However, despite its critical nature, the everyday experience of treating these patients is not systematically curated or analyzed outside of the expert's mind. To access this wealth of experiential knowledge today requires an in-person consultation with an expert whose availability and location have natural limits, and is mostly outpaced by patient demand. Short of these rare personal consultations, there is no way to take advantage of this invaluable resource today.

Registries and research cohorts are preliminary attempts to capture this experiential learning. For example, the SEER registry of the National Cancer Institute (NCI) is a standardized cancer registry that collects disease, treatment and outcome level information of cancer patients from across the country. However, registries are very limited, and only contain very high level information about each patient case and outcome, and are insufficient for decision making.

The solution presented herein uses a clinical informatics database, developed according to a structured ontology created by the inventors, and a machine learning approach to solve this problem by learning and predicting treatments for new patients based on experts' prior recommendations for similar patients. The widespread adoption of Electronic Medical Records (EMRs) allows for the curation of patient medical records to meet various objectives. In this instance, the records may be entered into a structured database based on data elements, both elements obtained directly from a patient's medical record (e.g., patient features, previous treatments and their responses, experts seen, experts' decisions, patient outcomes, etc.) and elements inferred from those present in the medical record (e.g., higher-level implications of the patient's condition, as explained in further detail below).

The solution also develops machine learning techniques that can automatically consider an untreated, patient, and recommend a treatment that would likely be recommended by a particular expert, based on the expert's prior pattern of treatment recommendations for patients that the system discovers are similar to the new patient, in both conventional and unconventional ways (the solution can also make such recommendations without respect to any given expert). Thus, in some embodiments, the system may include a structured database configured to predict clinical decisions prospectively and a machine learning system that can consider patient similarity grouped based on an outcome of interest (say expert decisions or treatments).

Architecture of the Solution

Figure 1:
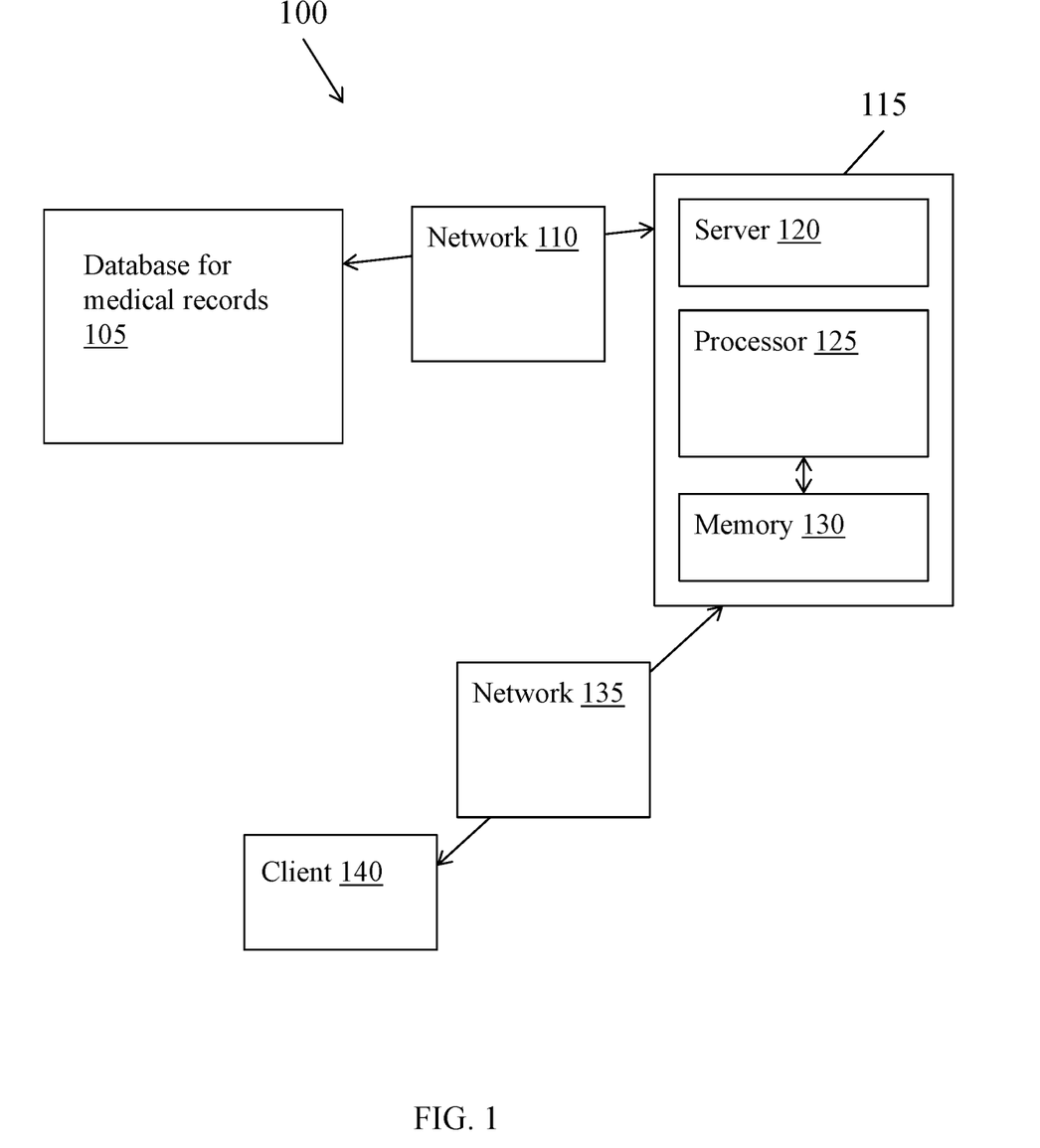
FIG. 1 depicts an exemplary system that implements the similarity-based treatment recommendation system described herein.

FIG. 1 depicts an exemplary architecture for implementing the similarity-based treatment system 100 described herein. The system 100 includes a database 105 that stores records of patients according to the inventors' ontology (whenever patient records are described herein, the records include the patients' medical records, but may also include other relevant information outside of the medical records themselves). The database 105 communicates over a computer network 110 with a server system 115, which includes one or more servers 120, each with one or more processors 125 and one or more memories 130 or other storage units (not shown). The server system 115 communicates over a computer network 135 (which can be the same network as network 110, or a different network) with a client 140. The client 140 may be a computing device that stores an untreated patient's record. Through the client, a user may transmit the untreated patient's record to the server system 115 and request a recommended treatment for the patient. The server system 115 may search the database 105 for the records of similar patients, as defined according to this disclosure, and identify a treatment from these records.

Overview of the Solution

Figure 2:
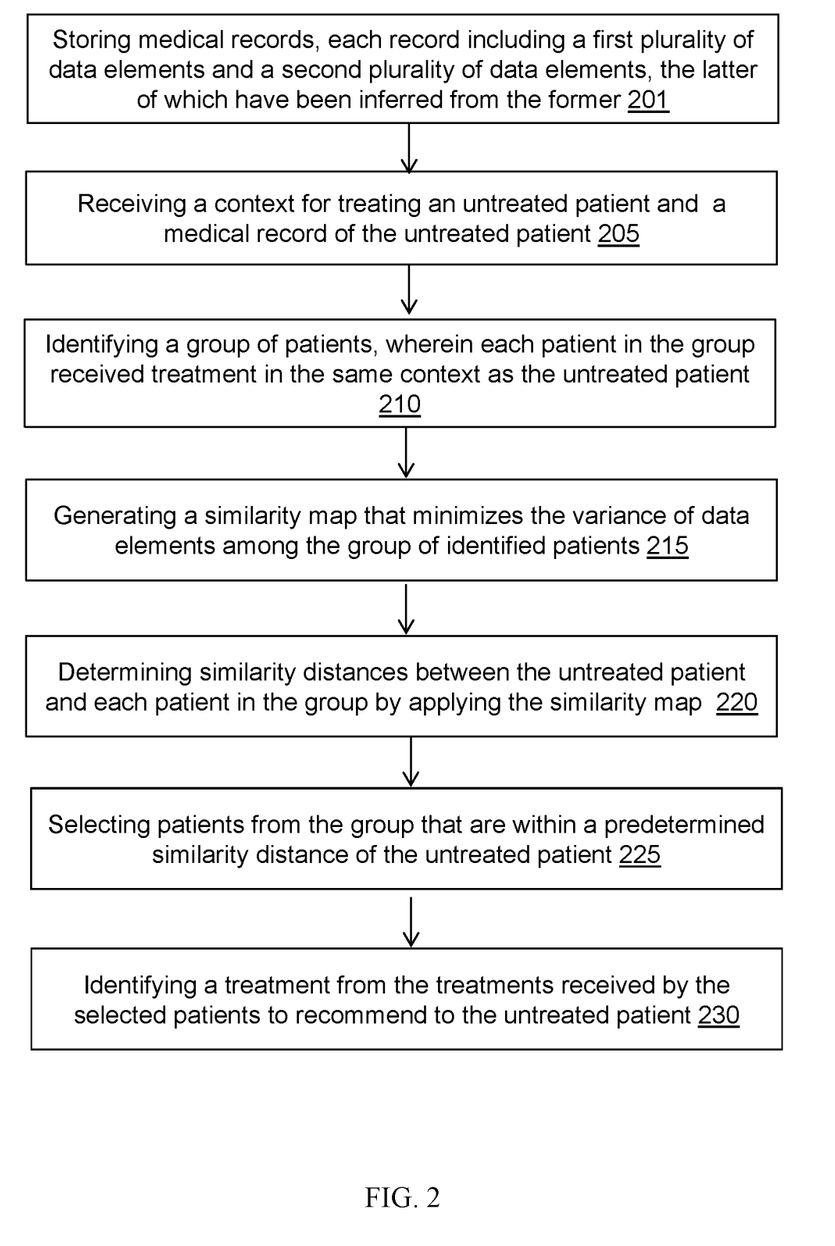
FIG. 2 depicts an exemplary flow diagram for a method of providing a treatment recommendation based on similar groups of patients.

FIG. 2 depicts an exemplary flow diagram for a method of providing a treatment recommendation based on similar groups of patients. The method includes storing records, each record including a first plurality of data elements and a second plurality of data elements, the latter of which have been inferred from the former (step 201). The method includes receiving a context for treating an untreated patient and a record of the untreated patient (step 205). The method includes identifying a group of patients, wherein each patient in the group received treatment in the same context as the untreated patient (step 210).

The method includes generating a similarity map that minimizes the variance of data elements among the group of identified patients (step 215). The method includes determining similarity distances between the untreated patient and each patient in the group by applying the similarity map (step 220). The method includes selecting patients from the group that are within a predetermined similarity distance of the untreated patient (step 225). The method includes identifying a treatment from the treatments received by the selected patients to recommend to the untreated patient (step 230).

Structured Ontology and Database of Records

The database 105 of the similarity-based treatment system 100 stores records of treated patients using an ontology (e.g., a set of prescribed terms and relationships) that is detailed, vast, interconnected, deductive, and mutable, thereby capturing clinical concepts in an unprecedented manner. The ontology begins with data elements that influence treatment decision making by experts, and the terms and relationships may be represented as fields, values, and rules in a computer system. Rather than being terms included with records as simple metadata, the data elements are structured, interconnected terms that convey simple and higher-level concepts present in any given record.

In some embodiments, terms for data elements may be grouped by patient conditions or characteristics, observations and/or test results about the patient, observations and/or test results about a disease (e.g., clinical, imaging, and pathological findings regarding a patient's tumor), prior and/or planned diagnostic and therapeutic interventions, morbidities or co-morbidities and related signs, responses to and side effects of therapies, experts who recommended treatment, and outcomes. Any given data element may be disease-specific, and data elements may further be interconnected with other diseases, or simply other data elements. In many embodiments, data elements may be information included in a patient's medical record. However, data elements may also encompass information related to the patient that would not appear in a medical record. Two such examples include the names of expert physicians and hospitals. Furthermore, data elements may be derived from sources such as raw medical reports.

Exemplary values for data elements may be as follows:
source level data—affiliations and/or bibiliography of the patient's case
patient related data—menopausal status, last menstrual period, time spent breastfeeding, heart function
disease level data—tumor size, anatomical location of the tumor, invasion of local structures, nerve invasion, CT scan findings
prior treatment related data—surgeries performed, response to therapy such as progressive disease
morbidity level data—complications of therapies, complaints and symptoms of the patient such as jaundice, swelling in the feet
planned treatment related data—dates of chemotherapy, dosages planned, support medications to be used
expert level data—expert names, education, specialties, experience
outcomes level data—alive with disease, complete response, partial response The similarity-based treatment system 100 may store definitions for any of these data elements in memory 130 or other storage. In some embodiments, the data elements and/or their definitions are derived from contents of individual records that have been analyzed either by humans or computer algorithms that search for terms and synonyms. Data elements in the ontology may be defined by evidence, guidelines, or by humans, like experts based on their experience.

Furthermore, using inference definitions that have also been stored in memory 130 or storage, the similarity-based treatment system 100 may infer additional data elements based on any of the data elements described above, and store these data elements in the patient's record. The inferred data elements may correspond to higher-level implications of the patient's condition than those conveyed by the exemplary data elements described above.

The following example demonstrates the distinction between the types of data elements thus described and how data elements may be created using inferences. Suppose a patient has jaundice, which is colloquially understood as yellowing of the skin. In the similarity-based treatment system 100, "jaundice" may be defined as a clinical observation that is related to a lab observation, namely, a high bilirubin level. The bilirubin levels may be low, normal, or high (each level being associated with particular ranges), the lab observation of "high bilirubin level" is also a diagnostic lab intervention. Further, the high bilirubin level is related to two separate clinical diagnoses: liver disease and hemolysis. In turn, liver disease is related to two clinical observations: infiltration of the liver and obstruction of the liver. Infiltration of the liver is related to the clinical condition of tumor infiltration or the clinical diagnosis of autoimmune disease. Obstruction of the liver is associated with two clinical conditions: obstruction within the liver or obstruction outside the liver. The patient record also mentions imaging observations of a gallbladder tumor and common bile duct enlargement. Lastly, the patient record also includes a lab observation of normal hemoglobin.

As this example demonstrates, the complexity of potential relationships between these pieces of information cannot be adequately uncovered and captured using simple predefined flow charts and rules. The number of variables and resulting rules would make this task unworkable. Given the granular level of the data elements, structured ontology and definitions of relationships (especially at an intelligent and high level) are required to decipher and connect interconnected relationships and logic.

Additionally, using its inference definitions, the similarity-based treatment system 100 may infer that the jaundice is related to the common bile duct enlargement and the gallbladder tumor. Because the hemoglobin is normal, the system 100 may further infer that the jaundice is not related to hemolysis, and since the liver appears normal on imaging, the system 100 may further infer that the jaundice is not related to liver infiltration.

This example simplifies a typical patient record. In practice, records may include significantly more data elements, both inferred and otherwise. For example, a single breast cancer record processed according to the inventors' ontology may include over 10,000 individual data elements about the patient, which may be linked together, and over 800 inferred data elements, which may be linked to the individual data elements, one another, or both.

In some embodiments, the server system 115 stores inference definitions in memory 130 or other storage. The processor 125 retrieves these definitions and applies them to the data elements for any given patient's record, thereby creating an expanded set of interconnected terms that may be stored with the record. These additional data elements may be represented as logical combinations of terms (e.g., data elements) with Boolean operators and nested hierarchies, directed acyclical graphs, or other decision trees.

Additionally, the server system 115 may adjust definitions of individual data elements and inferences as additional patient records are added to the database 105. For example, a newly added record may include a lab observation not included in previous records, or describe a treatment not previously applied to patients whose records have already been stored in the database. Furthermore, the similarity-based treatment system 100 is configured to add additional inference definitions, based on new records. For example, if the system 100 receives a record of a patient who has jaundice due to genetic problems, instead of liver infiltration, liver obstruction, or hemolysis, the system 100 may add and/or amend its inference definitions accordingly.

In some embodiments, records include all treatment decisions, which aids in discovering data elements at the most granular decision level. For example, records may store treatment decisions that were never executed, as well as treatment decisions that were implemented (for example, if a treatment was recommended, but was never taken, this is still captured as the decision making is of equal importance as the outcome of the treatment). Additionally, although data elements are described herein with the view towards recommending a treatment for a disease, data elements and inference definitions may be tailored for other purposes, such as diagnosing a disease or selecting doctors/hospitals/places of care.

The process of storing an unstructured record using the structured data elements important in decision making can be done either by human coders of the data, natural language processing (NLP) assisted human coding, or automated techniques alone. For example, a human annotator may identify the data elements in a patient record, including new terms that the annotator feeds into an NLP process to assess the term for inclusion into definitions stored in the server system 115. Additionally, in some embodiments, the original unstructured record may be also stored in the database 105 to provide a reference to mine for more discrete data elements that are discovered to be important at a later state. All of this data are collected both retrospectively and prospectively.

In some embodiments, after the data elements are known and records are stored in the database according to the inventors' ontology, weights are discovered and assigned to all the data elements by quantifying how much individual data elements contribute to changes in decision making. Similar to the discovery of these data elements themselves, the discovery of weights can be done through the observation and discussion with experts, evidence and guidelines, as well as using machine learning techniques. Through various mathematical methods, a list of weights for each data element can be discovered in the system 100 as a measure of how much any given element contributes to a particular decision made in a patient's case. These weights may depend on many factors, and may be unique for different experts with different characteristics or experience in treating different diseases, as well as different decision points in the course of a disease, and for different sets of treatment options. Thus, the weights or importance the data elements depends substantially entirely on who is taking the decision, the nature of the data elements, the decision being taken, among other factors. In some embodiments, weights are assigned based on the data elements' contribution to intra-group variance.

Learning Linear and Non-Linear Similarities Between Groups of Patients

Although conventional machine-based methods for identifying prospective treatments for patients rely on linear, demographic-based concepts of similarity (e.g., same age, gender, ethnicity, health history), the inventors have discovered that similarities can exist along non-linear, and thus non-obvious, data elements. Moreover, these previously unknown and unappreciated similarities can be exploited to discern which treatments may be more effective or appropriate than treatments that might be identified using linear similarities, alone.

For example, if two patients are matched in a conventional, linear manner, patients of age 10 would be deemed more similar to patients of age 30 rather than patients of age 80. However, if patients are considered in the context of vulnerability with respect to interventions (e.g., potential interactions with antibiotics or anesthesia, or surgical risk), patients of ages 10 and 80 might be considered high risk for complications, while patients of age 30 might be considered low risk. Thus, with respect to complications from interventions, age 30 is quite dissimilar to age 10. However, under conventional methods, the similarity between patients of ages 10 and 80 would be overlooked, and would be the underlying dissimilarity between patients of ages 10 and 30. In contrast, the inventors' solution would enable such similarities to be discovered and used in making treatment decisions.

The solution would even discover similarities between data elements that are normally considered unrelated in the ontology of the disease, given traditional approaches to measuring distances between the values of data elements. For example, patients with old age and smoking status may be similar to patients of any age or smoking status with diabetes, when related to a risk of poor healing after cancer surgery. There are many mathematical distances between multi-feature distributions, and appropriate distance metrics can be chosen based on the number and complexity of features in the particular dataset studied.

To learn non-linear similarities, patients are first grouped based on one or more data elements of interest, and the records of this group are processed to learn linear and non-linear similarities of various combinations of other data elements.

A. Grouping Patients

Moreover, because the database 105 stores thousands, and possibly millions, of records for patients, an appropriate group of patients must be obtained from the database for measures of similarity to be meaningful. Any such group must have values for at least one data element in common. For any given data element for which a recommendation is being sought, the data element(s) selected to have values in common may be pre-determined, or determined by machine learning that has been applied to the database 105 of records. Moreover, the data element for which a recommendation is being sought may be any type of data element normally received and entered into a patient's record, or any type of data element inferred from other elements in the record.

For example, in the context of selecting treatment for a patient, the data elements of interest may be clinical diagnosis, objective, timing, and/or setting. Thus, the server system 115 would retrieve from the database 105 records of patients who received the same clinical diagnosis and received treatment with the same objective (e.g., curative, control, palliative), timing (e.g., primary, adjuvant, neoadjuvant), and/or setting (e.g., first line, second line, induction, maintenance). The records may further be limited to treatments that are related to one another, or treatments that the patient is willing to undertake.

The group of patients may be further limited in any manner, and to any size, desired by the user of the system 100. For example, the user may limit the group to patients who received treatment recommendations by the same expert physician, or a group of similar expert physicians. In any case, the group is limited based solely on data elements recognized by the inventors' ontology. Moreover, the number of iterative steps to reduce the size of the group based on additional data elements may be driven solely by the final number of records to be considered. If the number becomes extremely small, the number of samples and high variance between them may hinder the accuracy of learned similarities. However, if the number is too large and cumbersome, the grouping may be inadequate such that non-linear similarities between data elements may fail to be uncovered, thereby collapsing into a model that is heavily reliant on linear similarities.

In one example, based on user instructions, the server system 115 searches the database 105 for the records of patients who had the same clinical diagnosis, From these records, the server system 115 extracts records for those who were treated by a particular expert physician, E1. The server system 115 further reduces this group to records of patients whose treatments share one or more particular characteristics, such as palliative care. In some embodiments, a user manually selects values for data elements to define the group of patients that will be used for comparison. Alternatively, the combinations of values for data elements may be obtained using an iterative machine learning process, or imported from data sources that include predetermined and known combinations of data element values that have been useful in other patients' cases.

Moreover, although the groups are chosen herein to obtain a recommended treatment, groups may also be chosen to obtain recommendations for other elements. For example, the group may be chosen so that the user may receive a recommendation for a hospital at which to receive care, an expert to render a treatment decision, a combination of hospital and treatment to select, or any other data element. In any of these situations, the system 100 first constrains the group of patients to those whose records include accepted values for the data element to predict (e.g., hospital, expert), and then further limits the group to obtain the size and variance desired.

B. Generating a Similarity Map Based on the Group of Patients

As described with respect to the inventors' ontology, any given record may include thousands of data elements. As a result, after a group of patients has been selected based on constraints posed by a user of the system 100 or machine learning, thousands of varying data elements may still remain, and many of them may not have a significant bearing upon treatment decisions. Thus, reducing the number of data elements to the lowest number of discrete yet influential data elements needed for decision making aids in determining similarity and reduces the computational time needed to make this determination. In some embodiments, relevant component analysis is applied to identify data elements with low variance within the group.

Exemplary approaches to relevant component analysis are explored in the following publications: Shental, N. et al., "Adjustment Learning and Relevant Component Analysis," Proc. European Conference on Computer Vision (ECCV), 2002, pp. 776-790; Sorci, M. et al., "Fisher's discriminant and relevant component analysis for static facial expression classification", 15th European Signal Processing Conference (EUSIPCO), 2007; Bar-Hillel, A. et al., "Learning Distance Functions using Equivalence Relations," Proc. International Conference on Machine Learning (ICML), 2003, pp. 11-18; Xing, E. et al., "Distance metric learning with application to clustering with side-information", Advances in Neural Information Processing Systems, 2002; Tsang, I. W. et al., "Kernel Relevant Component Analysis For Distance Metric Learning", International Joint Conference on Neural Networks, 2005; and Xing, E. et al., "Distance metric learning with application to clustering with side-information", Advances in Neural Information Processing Systems, 2002.

In further embodiments, the server system 115 may run machine learning algorithms or programs that learn from experts to identify data elements that are significant to decision making. For example, the system 100 may present the machine learning algorithms and/or experts with different data elements that vary in number and type until necessary and sufficient information is presented in the case and a decision is made. The inputs uncover the relative importance of particular data elements to decision making. Thus, even if expert physicians claim that 5 particular data elements are very important to their decisions, their inputs to the system 100 may reveal that information for only 2-3 of them leads to the same decisions as knowing all 5.

The server system 115 may use the reduced set of data elements to create the similarity map (or continue using the entire set of data elements, as desired). The map uncovers similarities between the remaining data elements that have not been constrained by the user of the system 100 or the server system 115 itself. In particular, the server system 115 generates a similarity map that minimizes the variance of data elements among the group of patients, which also reveals non-linear and thus unexpected similarities between the elements.

The server system 115 may generate the similarity map by first determining a locus for the group of patients, across all data elements. Conceptually, the locus represents a center for the group, and in various examples, the locus may be derived from the means of data elements for the patients. Each mean may be a sample mean, a windsorized mean, or any other type of mean. Moreover, each mean in the locus may be the same type of mean (e.g., sample mean). Alternatively, the different data elements may have different types of means.

The server system 115 may generate the similarity map by summing a function of the distance between the patients in the group and the locus. In this manner, the similarity map may represent the dispersion of the group. Suppose a group of patients has been limited to those who received treatment recommendations from a group of particular experts, and whose treatment fell within a group of related treatments, "$T_r$". In one embodiment, the similarity map may be expressed as:

$$MAP_\varepsilon = \frac{1}{\Omega}\sum_{a=1}^{T}(P(n) - P_a(y))(P(n) - P_a(y))^T$$

$$MR(n)\varepsilon T_{Ra}(e)$$

In which $\Omega$ is the number of patients in the group;
T is the treatment space;
$T_r$ is a group of related treatments in the treatment space;
a is a particular treatment;
$P(n)$ is the $n^{th}$ patient;
y is an expert; and
$P_a(y)$ is the locus of patients who have received the particular treatment
"a", within the treatment group $T_r$, at the hands of expert "e".

Consequently, the term $MR(n) \varepsilon T_{ra}(e)$ represents the group of patients used for the similarity map, namely, every patient with a record MR who received a treatment within the treatment group $T_r$, at the hands of expert "e".

Moreover, by accounting for variance among patient records and forcibly reducing some of the variance, the system 100 may reduce the variance of the similarity map. Exemplary approaches to reducing variance include eliminating outliers, performing relevant component analysis, using an epsilon ball, and comparing distributions to detect outliers, among others.

The weights that are previously learned can be iterated with the similarity step such that the map produces narrower and narrower measures of error in the predictions by eliminating the heterogeneity of groups with respect to important data elements.

Additionally, the server system 115 may generate a measure of confidence in the similarity map. The measure may correspond to the number of patients in the group that are within a certain pre-defined similarity (e.g., similarity distance) of the untreated patient. The more patients that are similar to the untreated patient, the more confidence in the frequency distribution of the various treatments in the pool of patients judged to be similar. Moreover, less variance in the types of treatments (e.g., a more skewed distribution towards one decision) may reflect greater precision, concordance and confidence of the experts in treatment decisions made for the group of patients. Thus, large databases with many patients in each grouping of treatment-expert or other data elements, combined with logical consistency of action by experts over a period of time, will produce the highest confidence in the results of the similarity map.

Because the inventors' ontology enables patients to be grouped in unique ways that enable non-linear similarities between data elements to be learned, other similarity maps or metrics that are derived from conventional techniques, such as k-means, may also be used. However, the combination of the inventors' ontology and the inventors' approach to finding similarities has proven to be a powerful and effective pairing.

Using the Learned Similarities to Select a Treatment

The server system 115 uses the similarity map to determine similarity distances between the untreated patient and each patient in the selected group. The manner in which such distances are determined depends on, among other things, the nature of the data for a particular expert or group of experts, in conjunction with the treatments that the expert(s) has prescribed for a particular clinical diagnosis. Use of the similarity map varies based on the nature of the data elements in the group of patients. For example, the data elements may be categorical, continuous, include imputed missing data, or have or lack calculable covariances. Depending on the situation, the similarity distances may be determined according to different methods. For example, distances may be determined using k-means approaches, Mahalanobis distances (e.g., for data elements that are continuous with covariances), Eskin distances, Goodall distances (e.g., with categorical data elements), and Lin distances, among others.

In one embodiment, the similarity distance between the untreated patient "p" and the patient from the group "$\hat{p}$" may be represented as:

$$SIM(p,\hat{p}) = \sqrt{(p-\hat{p})^T (MAP_e)^{-1} (p-\hat{p})}$$

After the server system 115 determines the similarity distances between the untreated patient and each patient in the group, the server system 115 may select patients from the group that are within a predetermined similarity distance from the untreated patient. For example, the user of the server system 115 may specify the threshold distance as a sensitivity or radius parameter R. If the server system 115 finds a low number of patients that fall within this distance R, the server system 115 may increase R until it includes a minimum number of patients, and then retrieves their records.

Alternatively, patients can be mapped to other patients in the database using any of the following methods:

a. exact or partial matches of all the data elements with weights for importance, b. different rules or combinations of the data elements of importance that create lower number of important data elements to match on rather than the high dimensions of the database, c. employing the similarity map in conjunction with the above two strategies, or by itself, d. patients with a minimum closest number to the untreated patient, or patients within a certain distance from the untreated patient, or a maximized function between the two can be chosen as well.

In some embodiments, a graph of the frequency of the desired outcome can be generated along with the confidence estimates surrounding each treatment option. If there are insufficient patients to give a meaningful conclusions for a given treatment, or for a given data element combination in a patient, that will also be manifest (e.g., threshold effect for the confidence).

The server system 115 may identify a treatment to recommend for the untreated patient based on the treatments received by the most similar patients. This decision may be made in any of several ways. For example, the server system 115 may choose the most commonly prescribed treatment, which would assure the maximum population level accuracy with respect to expert concordance. In some embodiments, the server system 115 may choose randomly from among the possible treatments, potentially increasing the fairness to an individual patient, by providing the opportunity to receive a less common treatment that may be more correct/relevant. In some embodiments, the server system 115 displays all of the treatments received by the selected patients, and the untreated patient and/or the healthcare provider may decide which treatment is best for the patient.

In some embodiments, the predictions of various experts are combined based on their expert weights. Experts may have multiple data elements that are collected into an expert medical practitioners database based on their own unique ontology and data structures. The data elements may include the direct fit/relevance to the patient being seen, their specialty, years of training, institute of training, how many similar patients the expert has seen before, how successful her outcomes, complications, side effects were, etc. Based on these data elements and matching them to the untreated patient, an expert weight is calculated and assigned much in the same way that the weights are assigned to data elements that contribute to decision making, as described above. Using these weights, illustrative embodiments can modify/combine the predictions of various experts, and also choose which experts should ideally be assigned to the untreated patient if so desired based on the learned outcomes of interest for a given untreated patient's disease and other characteristics.

Continuous new data elements preferably will be added into the database and assessed by machine learning for inclusion into the algorithms (high weights) and/or to assess for a match and confidence score with new client records.

Note that this approach above can be used for any intervention (including no intervention) that is a result of a consideration of data elements associated with a patient record according to some logical/medical principles. As such, the applications for sequencing and staging of decisions (surgery before or after chemotherapy) or (direct chemotherapy or sequential after a negative ultrasound) are an obvious benefit of this system. In addition, sequencing of diagnostic tests, as well as sequencing of which hospital/ expert to choose, can be accomplished in the same model. For inter-dependent sequential events (where the combination of two events produces a different probability/confidence in the decision that simply the sum of the two events), measures of additional probability changes can be modeled into the decision system using Bayesian decision modeling as one approach. Other approaches also may be used.

Discordance between the system's 100 decisions with the evidence, guidelines, live experts and patient preference can be exploited to see which data elements are most relevant for which knowledge source of decision making. This understanding also helps to combine the decisions from heterogeneous sources. Importantly, these methods can be applied towards appropriately fusing the information from evidence, guidelines, live experts, patient preference, the system 100 and other heterogeneous sources of information. If there is less confidence from one source, and more from the other based on the weights of the important data elements discovered for that decision, different sources of information can be weighed higher or lower allowing for fusing of heterogeneous sources of information.

Experiential knowledge therefore takes precedence for many diseases and treatments. Furthermore, for rare or uncommon diseases, or highly complex diseases requiring multi-disciplinary coordinated care, such as most cancer care, the amount of experience from patient volume and complexity that accumulates in specialized tertiary care centers is unparalleled in any single physician's office outside of these settings.

The system database stores the patient record along with detailed features such as a patient's prior treatments and the responses to those treatments, experts that are consulted, and the recommended treatments along with the outcomes of those treatments, in a structured format, according to the inventors' ontology. Using its machine learning algorithms as described above, the system 100 finds patients that are similar to an untreated patient, (optionally) matches the untreated patient's data elements of high importance for the chosen expert, and generates a profile of predicted decisions for the untreated patient based on a generated similarity map, and a decision of interest. These predictions are expected to directly impact millions of patients and extend the access of specialists well beyond the purview of large academic medical centers.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A method of selecting a treatment for a patient based on a group of patients of a population of patients, the method comprising:

storing, in a database, records for the population of patients, each record including a plurality of data elements including at least one treatment, and at least one of a clinical diagnosis, an objective, a procedural timing, or a setting;

receiving, by a server system, a record of an untreated patient;

generating a machine learning model by determining a plurality of data element clusters using the records of the population of patients including the at least one of the clinical diagnosis, the objective, the procedural timing, or the setting;

updating the machine learning model after receiving an update to the records of the population of patients;

determining a cluster of the plurality of data elements from the plurality of data element clusters of the updated machine learning model;

identifying, by the server system, the group of patients, wherein each patient in the group of patients received treatment in the same context as the untreated patient;

generating, by the server system, a similarity map that minimizes a variance of the cluster of the plurality of data elements for to the records of the group of patients;

determining, by the server system, a remaining cluster of the plurality of data elements using the similarity map, the remaining cluster of the plurality of data elements being interrelated by at least one non-linear similarity;

determining, by the server system, similarity distances between the untreated patient and each patient in the group of patients using the cluster of the plurality of data elements from the record of the untreated patient and the remaining cluster of the plurality of data elements for each patient in the group of patients;

selecting, by the server system, patients from the group of patients that are within a predetermined similarity distance of the untreated patient; and identifying, by the server system, the treatment from the treatments received by the selected patients to recommend to the untreated patient.

2. The method of claim 1, wherein storing the records for each patient of the population of patients comprises:

storing the plurality of data elements for the record of the patient, the plurality of data elements including conditions about the patient, observations about the patient, test results about the patient, clinical findings of the patient, obtained imaging about the patient, pathological findings of the patient, prior diagnosis, planned diagnostic interventions, prior therapeutic interventions, planned therapeutic interventions, morbidities, side effects of administered therapies, name of an expert physician, name of a hospital, or any combination thereof.

3. The method of claim 1, wherein storing the records for the population of patients comprises:

storing, for the record of each patient of the population of patients, the plurality of data elements as (i) logical combinations of terms using Boolean operators, (ii) nested hierarchies, or (iii) directed acyclical graphs.

4. The method of claim 1, wherein the objective includes a curative objective, a control objective, or a palliative objective.

5. The method of claim 1, wherein the procedural timing for treatment is primary, adjuvant, or neoadjuvant.

6. The method of claim 1, wherein identifying the group of patients comprises:

identifying, by the server system, the group of patients, wherein at least one data element of the plurality of data elements for each patient in the group of patients includes a same value.

7. The method of claim 6, wherein the plurality of data elements for each patient in the group of patients includes a treatment recommendation from the same expert.

8. The method of claim 6, wherein identifying the group of patients comprises:

constraining, by the server system, the population of patients to patients with values of additional data elements of the plurality of data elements in common until a number of patients reaches a minimum size.

9. The method of claim 1, wherein generating the similarity map comprises:

generating a locus of the group of patients, the locus representing average values across data elements for the group of patients; and summing a function of distances between the locus and each patient in the group of patients.

10. The method of claim 1, wherein identifying the treatment from the treatments received by the selected patients to recommend to the untreated patient comprises:

selecting the treatment most common among the selected patients.

11. The method of claim 1, wherein identifying the treatment from the treatments received by the selected patients to recommend to the untreated patient comprises:

selecting the treatment at random among the treatments received by the selected patients.

12. A computer program product for use on a computer system for selecting a treatment for a patient based on a group of patients of a population of patients, the computer program product comprising a tangible, non-transient computer usable medium having computer readable program code thereon, the computer readable program code comprising:

program code for storing, in a database, records for the population of patients, each record including a plurality of data elements including at least one treatment, and at least one of a clinical diagnosis, an objective, a procedural timing, or a setting;

program code for receiving, by a server system, a record of an untreated patient;

program code for generating a machine learning model by determining a plurality of data element clusters using the records of the population of patients including the at least one of the clinical diagnosis, the objective, the procedural timing, or the setting;

program code for updating the machine learning model after receiving an update to the records of the population of patients;

program code for determining a cluster of the plurality of data elements from the plurality of data element clusters of the updated machine learning model;

program code for identifying, by the server system, the group of patients, wherein each patient in the group of patients received treatment in the same context as the untreated patient;

program code for generating, by the server system, a similarity map that minimizes a variance of the cluster of the plurality of data elements for the records of the group of patients;

program code for determining, by the server system, a remaining cluster of the plurality of data elements using the similarity map, the remaining cluster of the plurality of data elements being interrelated by at least one non-linear similarity;

program code for determining, by the server system, similarity distances between the untreated patient and each patient in the group of patients using the cluster of the plurality of data elements from the record of the untreated patient and the remaining cluster of the plurality of data elements for each patient in the group of patients;

program code for selecting, by the server system, patients from the group of patients that are within a predetermined similarity distance of the untreated patient; and program code for identifying, by the server system, the treatment from the treatments received by the selected patients to recommend to the untreated patient.

13. The computer program product of claim 12, wherein storing the records for each patient of the population of patients comprises:

storing the plurality of data elements for the record of the patient, the plurality of data elements including conditions about the patient, observations about the patient, test results about the patient, clinical findings of the patient, obtained imaging about the patient, pathological findings of the patient, prior diagnosis, planned diagnostic interventions, prior therapeutic interventions, planned therapeutic interventions, morbidities, side effects of administered therapies, name of an expert physician, name of a hospital, or any combination thereof.

14. The computer program product of claim 12, wherein storing the records for the population of patients comprises:

storing, for the record of each patient of the population of patients, the plurality of data elements as (i) logical combinations of terms using Boolean operators, (ii) nested hierarchies, or (iii) directed acyclical graphs.

15. The computer program product of claim 12, wherein the objective includes a curative objective, a control objective, or a palliative objective.

16. The computer program product of claim 12, wherein the procedural timing for treatment is primary, adjuvant, or neoadjuvant.

17. The computer program product of claim 12, wherein identifying the group of patients comprises:
   identifying, by the server system, the group of patients, wherein at least one data element of the plurality of data elements for each patient in the group of patients includes a same value.

18. The computer program product of claim 17, wherein the plurality of data elements for each patient in the group of patients includes a treatment recommendation from the same expert.

19. The computer program product of claim 17, wherein identifying the group of patients comprises:
   constraining, by the server system, the population of patients to patients with values of additional data elements of the plurality of data elements in common until a number of patients reaches a minimum size.

20. The computer program product of claim 12, wherein generating the similarity map comprises:
   generating a locus of the group of patients, the locus representing average values across data elements for the group of patients; and
   summing a function of distances between the locus and each patient in the group of patients.

* * * * *